United States Patent
Almazrouei et al.

(10) Patent No.: US 12,262,738 B2
(45) Date of Patent: Apr. 1, 2025

(54) ULTRASONIC MIST INHALER

(71) Applicant: SHAHEEN INNOVATIONS HOLDING LIMITED, Abu Dhabi (AE)

(72) Inventors: Mohammed Alshaiba Saleh Ghannam Almazrouei, Abu Dhabi (AE); Imad Lahoud, Abu Dhabi (AE)

(73) Assignee: Shaheen Innovations Holding Limited, Abu Dhabi (AE)

( * ) Notice: Subject to any disclaimer, the term of this patent is extended or adjusted under 35 U.S.C. 154(b) by 244 days.

(21) Appl. No.: 17/772,347

(22) PCT Filed: Dec. 15, 2019

(86) PCT No.: PCT/IB2019/060806
§ 371 (c)(1),
(2) Date: Apr. 27, 2022

(87) PCT Pub. No.: WO2021/123865
PCT Pub. Date: Jun. 24, 2021

(65) Prior Publication Data
US 2022/0400745 A1    Dec. 22, 2022

(51) Int. Cl.
| | | |
|---|---|---|
| A24F 40/485 | (2020.01) | |
| A24B 15/167 | (2020.01) | |
| A24F 40/05 | (2020.01) | |
| A24F 40/10 | (2020.01) | |
| A24F 40/42 | (2020.01) | |
| A61M 11/00 | (2006.01) | |

(Continued)

(52) U.S. Cl.
CPC ............ *A24F 40/05* (2020.01); *A24B 15/167* (2016.11); *A24F 40/10* (2020.01); *A24F 40/42* (2020.01); *A24F 40/485* (2020.01); *B05B 17/0684* (2013.01); *A61M 11/005* (2013.01); *B05B 17/0646* (2013.01)

(58) Field of Classification Search
None
See application file for complete search history.

(56) References Cited

U.S. PATENT DOCUMENTS

| | | | |
|---|---|---|---|
| 4,119,096 | A | 10/1978 | Drews |
| 4,334,531 | A | 6/1982 | Reichl |
| 5,355,873 | A | 10/1994 | Del Bon |

(Continued)

FOREIGN PATENT DOCUMENTS

| | | |
|---|---|---|
| CN | 2648836 Y | 10/2004 |
| CN | 101648041 A | 2/2010 |

(Continued)

OTHER PUBLICATIONS

Official Notice of Rejection, JP Application No. 2022-561688 mailed Oct. 3, 2023 (with English translation); 8 pages.

(Continued)

*Primary Examiner* — Oscar C Jimenez
(74) *Attorney, Agent, or Firm* — Amedeo F. Ferraro, Esq.

(57) ABSTRACT

The invention relates to an ultrasonic mist inhaler (100), comprising a liquid reservoir structure (2) comprising a liquid chamber (21) adapted to receive liquid to be atomized, a sonication chamber (22) in fluid communication with the liquid chamber (21); wherein the liquid reservoir structure (2) comprises the sonication chamber (22).

13 Claims, 3 Drawing Sheets

(51) Int. Cl.
    *B05B 17/00*      (2006.01)
    *B05B 17/06*      (2006.01)

(56) References Cited

U.S. PATENT DOCUMENTS

| | | |
|---|---|---|
| 5,518,179 A | 5/1996 | Humberstone et al. |
| 5,551,416 A | 9/1996 | Stimpson |
| 5,894,841 A | 4/1999 | Voges |
| 5,950,619 A | 9/1999 | van der Linden |
| 6,011,345 A | 1/2000 | Murray |
| 6,040,560 A | 3/2000 | Fleischhauer |
| 6,402,046 B1 | 6/2002 | Loeser |
| 6,601,581 B1 | 8/2003 | Babaev |
| 6,679,436 B1 | 1/2004 | Onishi |
| 7,129,619 B2 | 10/2006 | Yang |
| 8,991,722 B2 | 3/2015 | Friend |
| 9,242,263 B1 | 1/2016 | Copeman |
| 9,278,365 B2 | 3/2016 | Banco |
| 9,415,412 B2 | 8/2016 | Kawashima |
| 9,687,029 B2 | 6/2017 | Liu |
| 9,687,627 B2 | 6/2017 | Gallem |
| 9,718,078 B1 | 8/2017 | Chau |
| 9,867,398 B2 | 1/2018 | Guo |
| 9,980,140 B1 | 5/2018 | Spencer |
| 10,034,495 B2 | 7/2018 | Alarcon |
| 10,071,391 B2 | 9/2018 | Yu |
| 10,195,368 B2 | 2/2019 | Wang |
| 10,300,225 B2 | 5/2019 | Terry |
| 10,327,479 B2 | 6/2019 | Popplewell |
| 10,328,218 B2 | 6/2019 | Reed |
| 10,412,996 B2 | 9/2019 | Bright |
| 10,506,827 B2 | 12/2019 | Liu |
| 10,561,803 B2 | 2/2020 | Liu |
| 10,617,150 B2 | 4/2020 | Cameron |
| 10,757,971 B2 | 9/2020 | Liu |
| 11,039,641 B2 | 6/2021 | Liu |
| 11,207,711 B2 | 12/2021 | Hejazi |
| 11,219,245 B2 | 1/2022 | Liu |
| 11,278,055 B2 | 3/2022 | Liu |
| 11,304,451 B2 | 4/2022 | Hejazi |
| 11,324,253 B2 | 5/2022 | Liu |
| 11,431,242 B2 | 8/2022 | Liu |
| 11,517,685 B2 | 12/2022 | Danek |
| 11,589,609 B2 | 2/2023 | Liu |
| 11,641,876 B2 | 5/2023 | Liu |
| 11,690,963 B2 | 7/2023 | Danek |
| 11,700,881 B2 | 7/2023 | Liu |
| 11,730,896 B2 | 8/2023 | Hutchins |
| 11,744,282 B2 | 9/2023 | Liu |
| 11,744,284 B2 | 9/2023 | Liu |
| 11,771,133 B2 | 10/2023 | Lin |
| 11,771,137 B2 | 10/2023 | Liu |
| 11,796,732 B2 | 10/2023 | Novak, III |
| 11,877,600 B2 * | 1/2024 | Liu .................. A24F 40/49 |
| 11,964,301 B2 | 4/2024 | Hejazi |
| 2002/0129813 A1 | 9/2002 | Litherland |
| 2003/0164545 A1 | 9/2003 | Nadd |
| 2003/0192532 A1 | 10/2003 | Hopkins |
| 2003/0209005 A1 | 11/2003 | Fenn |
| 2006/0243277 A1 | 11/2006 | Denyer |
| 2006/0243820 A1 | 11/2006 | Ng |
| 2007/0125370 A1 | 6/2007 | Denyer |
| 2008/0054091 A1 | 3/2008 | Babaev |
| 2008/0088202 A1 | 4/2008 | Duru |
| 2008/0156320 A1 | 7/2008 | Low |
| 2008/0164339 A1 | 7/2008 | Duru |
| 2009/0022669 A1 | 1/2009 | Waters |
| 2009/0065600 A1 | 3/2009 | Tranchant |
| 2010/0084488 A1 | 4/2010 | Mahoney, III |
| 2010/0139652 A1 | 6/2010 | Lipp |
| 2011/0012677 A1 | 1/2011 | Lutsen Lundgerus |
| 2012/0126041 A1 | 5/2012 | Mahito et al. |
| 2013/0220315 A1 | 8/2013 | Conley |
| 2014/0007864 A1 | 1/2014 | Gordon |
| 2014/0151457 A1 | 6/2014 | Wilkerson |
| 2014/0261414 A1 | 9/2014 | Weitzel |
| 2014/0270727 A1 | 9/2014 | Ampolini |
| 2015/0069146 A1 | 3/2015 | Lowy |
| 2015/0202387 A1 | 7/2015 | Yu |
| 2015/0230522 A1 | 8/2015 | Horn |
| 2015/0231347 A1 | 8/2015 | Gumaste |
| 2015/0272214 A1 | 10/2015 | Giller |
| 2016/0001316 A1 | 1/2016 | Friend |
| 2016/0066619 A1 | 3/2016 | Di Carlo |
| 2016/0089508 A1 | 3/2016 | Smith |
| 2016/0198770 A1 | 7/2016 | Alarcon |
| 2016/0199594 A1 | 7/2016 | Finger |
| 2016/0206001 A1 | 7/2016 | Eng |
| 2016/0213866 A1 | 7/2016 | Tan |
| 2016/0264290 A1 | 9/2016 | Hafer |
| 2016/0324212 A1 | 11/2016 | Cameron |
| 2016/0331022 A1 | 11/2016 | Cameron |
| 2016/0338407 A1 | 11/2016 | Kerdemelidis |
| 2017/0042242 A1 | 2/2017 | Hon |
| 2017/0119052 A1 | 5/2017 | Williams |
| 2017/0119059 A1 | 5/2017 | Zuber |
| 2017/0135411 A1 | 5/2017 | Cameron |
| 2017/0136194 A1 | 5/2017 | Cameron |
| 2017/0136484 A1 | 5/2017 | Wilkerson |
| 2017/0251718 A1 | 9/2017 | Armoush |
| 2017/0265521 A1 | 9/2017 | Do |
| 2017/0281883 A1 | 10/2017 | Li |
| 2017/0303594 A1 | 10/2017 | Cameron |
| 2017/0368273 A1 | 12/2017 | Rubin |
| 2018/0042306 A1 | 2/2018 | Atkins |
| 2018/0153217 A1 | 6/2018 | Liu |
| 2018/0160737 A1 | 6/2018 | Verleur |
| 2018/0166981 A1 | 6/2018 | Leppard |
| 2018/0192702 A1 | 7/2018 | Li |
| 2018/0269867 A1 | 9/2018 | Terashima |
| 2018/0029677 A1 | 10/2018 | Terry |
| 2018/0286207 A1 | 10/2018 | Baker |
| 2018/0296777 A1 | 10/2018 | Terry |
| 2018/0296778 A1 | 10/2018 | Hacker |
| 2018/0310625 A1 | 11/2018 | Alarcon |
| 2018/0338532 A1 | 11/2018 | Verleur |
| 2018/0343926 A1 | 12/2018 | Wensley |
| 2019/0056131 A1 | 2/2019 | Warren |
| 2019/0098935 A1 | 4/2019 | Phan |
| 2019/0116863 A1 | 4/2019 | Dull |
| 2019/0133186 A1 | 5/2019 | Fraser |
| 2019/0158938 A1 | 5/2019 | Bowen |
| 2019/0166913 A1 | 6/2019 | Trzecieski |
| 2019/0167923 A1 | 6/2019 | Kessler |
| 2019/0216135 A1 | 7/2019 | Guo |
| 2019/0255554 A1 | 8/2019 | Selby |
| 2019/0289914 A1 | 9/2019 | Liu |
| 2019/0289915 A1 | 9/2019 | Heidl |
| 2019/0289918 A1 | 9/2019 | Hon |
| 2019/0321570 A1 | 10/2019 | Rubin |
| 2019/0329281 A1 | 10/2019 | Lin |
| 2019/0335580 A1 | 10/2019 | Lin |
| 2019/0336710 A1 | 11/2019 | Yamada |
| 2019/0037473 A1 | 12/2019 | Chen |
| 2019/0373679 A1 | 12/2019 | Fu |
| 2019/0374730 A1 | 12/2019 | Chen |
| 2019/0387795 A1 | 12/2019 | Fisher |
| 2020/0000143 A1 | 1/2020 | Anderson |
| 2020/0000146 A1 | 1/2020 | Anderson |
| 2020/0009600 A1 | 1/2020 | Tan |
| 2020/0016344 A1 | 1/2020 | Scheck |
| 2020/0022416 A1 | 1/2020 | Alarcon |
| 2020/0046030 A1 | 2/2020 | Krietzman |
| 2020/0068949 A1 | 3/2020 | Rasmussen |
| 2020/0085100 A1 | 3/2020 | Hoffman |
| 2020/0120989 A1 | 4/2020 | Danek |
| 2020/0120991 A1 | 4/2020 | Hatton |
| 2020/0146361 A1 | 5/2020 | Silver |
| 2020/0178598 A1 | 6/2020 | Mitchell |
| 2020/0178606 A1 | 6/2020 | Liu |
| 2020/0214349 A1 | 7/2020 | Liu |
| 2020/0221771 A1 | 7/2020 | Atkins |
| 2020/0221776 A1 | 7/2020 | Liu |
| 2020/0245692 A1 | 8/2020 | Cameron |

(56) References Cited

U.S. PATENT DOCUMENTS

| | | |
|---|---|---|
| 2020/0345058 A1 | 11/2020 | Bowen |
| 2020/0404975 A1 | 12/2020 | Chen |
| 2021/0015957 A1 | 1/2021 | Bush |
| 2021/0076733 A1* | 3/2021 | Liu .................. B05B 17/0684 |
| 2021/0112858 A1 | 4/2021 | Liu |
| 2021/0120880 A1 | 4/2021 | Liu |
| 2021/0153548 A1 | 5/2021 | Twite |
| 2021/0153549 A1 | 5/2021 | Twite |
| 2021/0153564 A1 | 5/2021 | Hourmand |
| 2021/0153565 A1 | 5/2021 | Twite |
| 2021/0153566 A1 | 5/2021 | Hourmand |
| 2021/0153567 A1 | 5/2021 | Twite |
| 2021/0153568 A1 | 5/2021 | Twite |
| 2021/0153569 A1 | 5/2021 | Twite |
| 2021/0177056 A1 | 6/2021 | Yilmaz |
| 2021/0212362 A1* | 7/2021 | Liu .................. A24F 40/42 |
| 2021/0378303 A1 | 12/2021 | Liu |
| 2021/0401061 A1 | 12/2021 | Davis |
| 2022/0030942 A1 | 2/2022 | Lord |
| 2022/0151301 A1 | 5/2022 | Liu |
| 2022/0240589 A1 | 8/2022 | Liu |
| 2022/0273037 A1 | 9/2022 | Liu |
| 2022/0279857 A1 | 9/2022 | Liu |
| 2022/0287361 A1 | 9/2022 | Kim |
| 2022/0295876 A1 | 9/2022 | Liu |
| 2022/0395023 A1 | 12/2022 | Liu |
| 2022/0400747 A1 | 12/2022 | Liu |
| 2023/0001107 A1 | 1/2023 | Connolly |
| 2023/0013741 A1 | 1/2023 | Liu |
| 2023/0020762 A1 | 1/2023 | Liu |
| 2023/0165303 A1 | 6/2023 | Liu |
| 2023/0292839 A1 | 9/2023 | Kim |

FOREIGN PATENT DOCUMENTS

| | | |
|---|---|---|
| CN | 104055225 A | 9/2014 |
| CN | 104082853 A | 10/2014 |
| CN | 204070580 U | 1/2015 |
| CN | 104640708 | 5/2015 |
| CN | 204499481 U | 7/2015 |
| CN | 105747277 A | 7/2016 |
| CN | 105768238 A | 7/2016 |
| CN | 105795526 A | 7/2016 |
| CN | 105876873 A | 8/2016 |
| CN | 205432145 U | 8/2016 |
| CN | 106108118 A | 11/2016 |
| CN | 205831074 A | 12/2016 |
| CN | 106422005 | 2/2017 |
| CN | 205947130 U | 2/2017 |
| CN | 206025223 U | 3/2017 |
| CN | 206043451 U | 3/2017 |
| CN | 206079025 U | 4/2017 |
| CN | 206119183 U | 4/2017 |
| CN | 206119184 U | 4/2017 |
| CN | 106617319 A | 5/2017 |
| CN | 206303211 U | 7/2017 |
| CN | 206333372 U | 7/2017 |
| CN | 107048479 A | 8/2017 |
| CN | 206586397 U | 10/2017 |
| CN | 206949536 U | 2/2018 |
| CN | 107822195 | 3/2018 |
| CN | 207185926 | 4/2018 |
| CN | 105476071 | 5/2018 |
| CN | 207383536 | 5/2018 |
| CN | 207400330 | 5/2018 |
| CN | 108283331 A | 7/2018 |
| CN | 108355210 A | 8/2018 |
| CN | 105876873 B | 12/2018 |
| CN | 109619655 A | 1/2019 |
| CN | 208354603 | 1/2019 |
| CN | 208434721 U | 1/2019 |
| CN | 106108118 B | 4/2019 |
| CN | 208837110 U | 5/2019 |
| CN | 209060228 U | 7/2019 |
| CN | 110150760 A | 8/2019 |
| CN | 209255084 U | 8/2019 |
| CN | 105876870 B | 11/2019 |
| CN | 209900345 U | 1/2020 |
| CN | 210076566 U | 2/2020 |
| CN | 210225387 | 3/2020 |
| CN | 110946315 A | 4/2020 |
| CN | 111229528 | 6/2020 |
| CN | 111838775 | 10/2020 |
| CN | 211675730 U | 10/2020 |
| CN | 212441811 | 2/2021 |
| CN | 214289213 | 9/2021 |
| CN | 214483267 | 10/2021 |
| CN | 215819888 | 2/2022 |
| CN | 217342045 | 9/2022 |
| CN | 217609513 | 10/2022 |
| CN | 217643921 U | 10/2022 |
| CN | 115336802 | 11/2022 |
| CN | 217826736 | 11/2022 |
| CN | 116807059 | 9/2023 |
| CN | 116650853 | 10/2023 |
| DE | 2656370 A1 | 6/1978 |
| DE | 2656370 B2 | 11/1978 |
| DE | 2656370 C3 | 7/1979 |
| DE | 100 51 792 A1 | 5/2002 |
| DE | 10122065 A1 | 12/2002 |
| EP | 0 258 637 A1 | 3/1988 |
| EP | 0 295 122 A2 | 12/1988 |
| EP | 0 258 637 B1 | 6/1990 |
| EP | 0 442 510 A1 | 8/1991 |
| EP | 0 442 510 B1 | 1/1995 |
| EP | 0 516 565 B1 | 4/1996 |
| EP | 0 824 927 A | 2/1998 |
| EP | 0 833 695 A1 | 4/1998 |
| EP | 0 845 220 A1 | 6/1998 |
| EP | 0 893 071 A1 | 1/1999 |
| EP | 0 970 627 A1 | 1/2000 |
| EP | 1083952 B1 | 12/2005 |
| EP | 1 618 803 B1 | 12/2008 |
| EP | 3 088 007 A1 | 11/2016 |
| EP | 3 192 381 A1 | 7/2017 |
| EP | 3 278 678 A1 | 2/2018 |
| EP | 3298912 A1 | 3/2018 |
| EP | 3 088 007 B1 | 11/2018 |
| EP | 3 434 118 A1 | 1/2019 |
| EP | 3 469 927 A1 | 4/2019 |
| EP | 3 505 098 | 7/2019 |
| EP | 3 520 634 A1 | 8/2019 |
| EP | 3 278 678 B1 | 10/2019 |
| EP | 3545778 A1 | 10/2019 |
| EP | 3 574 902 A1 | 12/2019 |
| EP | 3 516 971 | 3/2021 |
| EP | 3 528 651 | 5/2021 |
| EP | 3 837 999 A1 | 6/2021 |
| EP | 3 574 778 | 7/2021 |
| EP | 3 593 656 | 10/2021 |
| EP | 4252561 | 10/2023 |
| EP | 4033927 | 11/2023 |
| FR | 3043576 A1 | 5/2017 |
| FR | 3064502 A1 | 5/2018 |
| GB | 1 528 391 A | 10/1978 |
| GB | 2566766 A | 3/2019 |
| GB | 2570439 A | 7/2019 |
| JP | 05093575 U | 12/1993 |
| JP | 2579614 Y2 | 8/1998 |
| JP | 2001069963 A | 3/2001 |
| JP | 2005288400 A | 10/2005 |
| JP | 2008-104966 A | 5/2008 |
| JP | 2011-500160 | 1/2011 |
| JP | 2012-507208 | 3/2012 |
| JP | 2014-004042 | 1/2014 |
| JP | 2019515684 | 6/2019 |
| JP | 2019521671 A | 8/2019 |
| JP | 2019-524113 | 9/2019 |
| JP | 2019-526240 | 9/2019 |
| JP | 2019-526241 | 9/2019 |
| JP | 2020535846 A | 12/2020 |
| JP | 2022032444 | 2/2022 |
| KR | 20120107219 A | 10/2012 |
| KR | 210-2013-0052119 | 5/2013 |

(56) References Cited

FOREIGN PATENT DOCUMENTS

| | | |
|---|---|---|
| KR | 10-2013-0095024 | 8/2013 |
| KR | 20230024816 | 2/2023 |
| KR | 20230115452 | 8/2023 |
| KR | 20230123537 | 8/2023 |
| KR | 102584559 | 10/2023 |
| KR | 102587103 | 10/2023 |
| WO | WO 92/21332 A1 | 12/1992 |
| WO | WO9309881 | 5/1993 |
| WO | WO 2000/050111 A | 8/2000 |
| WO | WO 2002/055131 A2 | 7/2002 |
| WO | 02094342 A2 | 11/2002 |
| WO | WO 2003/055486 A | 7/2003 |
| WO | WO 2003/0101454 A | 12/2003 |
| WO | WO 2004/080216 | 9/2004 |
| WO | WO 2007/083088 A1 | 7/2007 |
| WO | WO 2008/076717 A1 | 6/2008 |
| WO | WO 2009/096346 A1 | 8/2009 |
| WO | WO 2012/062600 A1 | 5/2012 |
| WO | WO 2012/138835 A2 | 10/2012 |
| WO | WO 2013/028934 A1 | 2/2013 |
| WO | WO 2014/182736 A1 | 11/2014 |
| WO | WO 2015/128499 A1 | 3/2015 |
| WO | WO2015/084544 A1 | 6/2015 |
| WO | WO 2015/115006 A1 | 8/2015 |
| WO | WO 2016/010864 A1 | 1/2016 |
| WO | WO 2016/116386 | 7/2016 |
| WO | WO 2016/118941 A1 | 7/2016 |
| WO | WO 2016/175720 A1 | 11/2016 |
| WO | WO 2016/196915 A1 | 12/2016 |
| WO | WO 2017/076590 A1 | 5/2017 |
| WO | WO 2017/108268 A1 | 6/2017 |
| WO | WO 2017/143515 A1 | 8/2017 |
| WO | WO 2017/177159 A3 | 10/2017 |
| WO | WO 2017/197704 A1 | 11/2017 |
| WO | WO 2017/205692 | 11/2017 |
| WO | 2017/206212 A1 | 12/2017 |
| WO | WO 2017/206022 A1 | 12/2017 |
| WO | WO 2017/215221 A1 | 12/2017 |
| WO | 2018/000761 A1 | 1/2018 |
| WO | 2018/000829 A1 | 1/2018 |
| WO | 2018/032672 A1 | 2/2018 |
| WO | WO 2018/023920 A1 | 2/2018 |
| WO | WO2018/027189 A2 | 2/2018 |
| WO | 2018/040380 A1 | 3/2018 |
| WO | WO 2018/041106 A1 | 3/2018 |
| WO | 2018/058884 A1 | 4/2018 |
| WO | WO 2018/111843 | 6/2018 |
| WO | WO 2018/113669 A1 | 6/2018 |
| WO | WO 2018/115781 A1 | 6/2018 |
| WO | WO 2018/163366 A1 | 9/2018 |
| WO | WO 2018/167066 | 9/2018 |
| WO | 2018/188616 A1 | 10/2018 |
| WO | 2018/188638 A1 | 10/2018 |
| WO | WO 2018/211252 A1 | 11/2018 |
| WO | WO 2018/220586 A2 | 12/2018 |
| WO | WO2018/220599 A1 | 12/2018 |
| WO | WO 2019/016681 | 1/2019 |
| WO | WO 2019/048749 A1 | 3/2019 |
| WO | WO 2019/052506 A1 | 3/2019 |
| WO | WO 2019/052574 A1 | 3/2019 |
| WO | WO 2019/069160 A1 | 4/2019 |
| WO | WO 2019/138076 A1 | 7/2019 |
| WO | WO 2019/173923 | 9/2019 |
| WO | WO 2019/198688 | 10/2019 |
| WO | WO 2019/211324 | 11/2019 |
| WO | WO 2019/238064 | 12/2019 |
| WO | WO 2019/242746 A1 | 12/2019 |
| WO | WO 2020/019030 A1 | 1/2020 |
| WO | WO 2020/048437 A1 | 3/2020 |
| WO | WO 2020/057636 A2 | 3/2020 |
| WO | WO2020187138 A1 | 9/2020 |
| WO | WO 2020/225534 A1 | 11/2020 |
| WO | WO 2020/227717 | 11/2020 |
| WO | WO 2020/254862 A1 | 12/2020 |
| WO | WO 2021/036827 A1 | 3/2021 |
| WO | WO 2021/205158 | 10/2021 |
| WO | WO2022/104246 | 5/2022 |
| WO | WO2022/200151 | 9/2022 |
| WO | WO2022/203187 | 9/2022 |
| WO | WO 2023/018059 | 2/2023 |
| WO | WO2023/143058 | 8/2023 |
| WO | WO2023/179691 | 9/2023 |
| WO | WO2023/249371 | 12/2023 |

OTHER PUBLICATIONS

Extended European Search Report mailed May 8, 2023 for co-pending European Application No. 19956956.7, 9 pages.
Akira Kubo, Part 1: What is Personal Authentication?—The Last Resort for Internet Security—Series: Re-Introduction to PKI, Japan, @IT, Apr. 5, 2003; https://atmarkit.itmedia.co.jp/fsecurity/rensai/re_pki01.html (newly cited reference showing well-known technique) (No English version).
ISR and Written Opinion mailed Nov. 4, 2020 for International Application No. PCT/IB2019/060806.
ISR and Written Opinion mailed Nov. 4, 2020 for International Application No. PCT/IB2019/060807.
ISR and Written Opinion mailed Oct. 20, 2020 for International Application No. PCT/IB2019/060809.
ISR and Written Opinion mailed Mar. 10, 2022 for Intl. Appl. No. PCT/GB2021053312.
ISR and Written Opinion mailed Mar. 10, 2022 for Intl. Appl. No. PCT/GB2021053311.
ISR and Written Opinion mailed Mar. 10, 2022 for Intl. Appl. No. PCT/GB2021053316.
UKIPO Search Report dated Nov. 24, 2021 for Application No. GB2111261.0.
UKIPO Search Report dated Nov. 24, 2021 for Application No. GB2113658.5.
UKIPO Search Report dated Nov. 24, 2021 for Application No. GB2113623.9.
EPO Search Report dated Nov. 12, 2021 for corresponding European Application No. 19870060.1.
EPO Search Report dated Oct. 27, 2021 for corresponding European Application No. 19870058.5.
International Search Report and Written Opinion for International Appl. No. PCT/GB2021/050842 mailed Jul. 5, 2021.
International Search Report and Written Opinion for International Appl. No. PCT/GB2021/050817 mailed Jun. 17, 2021.
UKIPO Search Report for UK Appl. No. GB2104872.3 dated Jun. 25, 2021.
EPO Search Report and Search Opinion for International Appl. No. PCT/IB2019/060812 dated Jun. 22, 2021.
Extended European Search Report and Search Opinion for corresponding EP Application No. 20214228.7 dated May 26, 2021.
International Search Report and Written Opinion for International Appl. No. PCT/IB2019/055192 dated Apr. 29, 2020.
International Search Report for corresponding PCT Application No. PCT/GB2020/053219 mailed Mar. 31, 2021.
Written Opinion mailed Nov. 10, 2020 for corresponding International Application No. PCT/IB2019/060812.
International Search Report mailed Nov. 10, 2020 for corresponding International Application No. PCT/IB2019/060812.
EPO Search Report mailed Nov. 9, 2020 for corresponding EPO Application No. 19870059.3 (PCT/IB2019/060808).
Written Opinion mailed Oct. 20, 2020 for corresponding International Application No. PCT/IB2019/060811.
International Search Report mailed Oct. 20, 2020 for corresponding International Application No. PCT/IB2019/060811.
Written Opinion mailed Oct. 19, 2020 for corresponding International Application No. PCT/IB2019/060810.
International Search Report mailed Oct. 19, 2020 for corresponding International Application No. PCT/IB2019/060810.
EPO Search Report dated Sep. 16, 2020 for corresponding EPO Application No. 20168231.
Extended EPO Search Report mailed Sep. 15, 2020 for corresponding EPO Application No. 20168938.7.

(56) References Cited

OTHER PUBLICATIONS

Written Opinion mailed Jun. 25, 2020 for corresponding International Application No. PCT/IB2019/060808.
International Search Report mailed Jun. 25, 2020 for corresponding International Application No. PCT/IB2019/060808.
Written Opinion mailed Apr. 29, 2020 for corresponding International Application No. PCT/IB2019/055192.
International Search Report mailed Apr. 29, 2020 for corresponding International Application No. PCT/IB2019/055192.
EPO search report dated Sep. 20, 2017 for corresponding EPO Application No. 20168245.7.
EPO Supplementary Search Report for EPO Application No. EP 3 278 678 A4 dated Oct. 4, 2018.
International Search Report for International Appl. No. WO 2017/177159 A3 mailed Sep. 26, 2017.
EPO Supplementary Search Report for EPO Application No. EP 1 618 803 A4 dated Jul. 27, 2007.
Office Action, co-pending KR 10-2022-7024456 Dec. 22, 2023; 10 pages. (with English translation).
Notice of Allowance issued Aug. 19, 2024 for co-pending KR Application No. 10-2022-7024456; 6 pages.
Official Notice of Rejection mailed Jun. 4, 2024 for co-pending JP Application No. 2022-561688; 4 pages (with English translation).

\* cited by examiner

ULTRASONIC MIST INHALER

This application is a National Phase Application under 35 U.S.C. §371 of PCT/IB2019/060806, filed Dec. 15, 2019 (published on Jun. 24, 2021 as WO 2021/123865 A1) the entire contents of which are incorporated herein by reference.

FIELD OF THE DISCLOSED TECHNOLOGY

The invention relates to an ultrasonic mist inhaler for atomizing a liquid by ultrasonic vibrations.

BACKGROUND

Electronic vaporizing inhalers are becoming popular among smokers who also want to avoid the tar and other harsh chemicals associated with traditional cigarettes and who wish to satisfy the craving for nicotine. Electronic vaporizing inhalers may contain liquid nicotine, which is typically a mixture of nicotine oil, a solvent, water, and often flavoring. When the user draws, or inhales, on the electronic vaporizing inhaler, the liquid nicotine is drawn into a vaporizer where it is heated into a vapor. As the user draws on the electronic vaporizing inhaler, the vapor containing the nicotine is inhaled. Such electronic vaporizing inhalers may have medical purpose.

Electronic vaporizing inhalers and other vapor inhalers typically have similar designs. Most electronic vaporizing inhalers feature a liquid nicotine reservoir with an interior membrane, such as a capillary element, typically cotton, that holds the liquid nicotine so as to prevent leaking from the reservoir. Nevertheless, these cigarettes are still prone to leaking because there is no obstacle to prevent the liquid from flowing out of the membrane and into the mouthpiece. A leaking electronic vaporizing inhaler is problematic for several reasons. As a first disadvantage, the liquid can leak into the electronic components, which can cause serious damage to the device. As a second disadvantage, the liquid can leak into the electronic vaporizing inhaler mouthpiece, and the user may inhale the unvaporized liquid.

Electronic vaporizing inhalers are also known for providing inconsistent doses between draws. The aforementioned leaking is one cause of inconsistent doses because the membrane may be oversaturated or undersaturated near the vaporizer. If the membrane is oversaturated, then the user may experience a stronger than desired dose of vapor, and if the membrane is undersaturated, then the user may experience a weaker than desired dose of vapor. Additionally, small changes in the strength of the user's draw may provide stronger or weaker doses. Inconsistent dosing, along with leaking, can lead to faster consumption of the vaping liquid.

Additionally, conventional electronic vaporizing inhalers tend to rely on inducing high temperatures of a metal heating component configured to heat a liquid in the e-cigarette, thus vaporizing the liquid that can be breathed in. Problems with conventional electronic vaporizing inhalers may include the possibility of burning metal and subsequent breathing in of the metal along with the burnt liquid. In addition, some may not prefer the burnt smell caused by the heated liquid.

Electronic vaporizing inhalers are generally designed so that the liquid nicotine reservoir is arranged away from the metal heating component to prevent heating the unused liquid in the reservoir. This arrangement makes the inhaler device cumbersome and more complex to produce.

Thus, a need exists in the art for an electronic vaporizing inhaler that is better able to withstand these disadvantages.

BRIEF SUMMARY

According to one aspect of the invention, an ultrasonic mist inhaler, comprises:
- a liquid reservoir structure comprising a liquid chamber adapted to receive liquid to be atomized,
- a sonication chamber in fluid communication with the liquid chamber,
- wherein the liquid reservoir structure comprises the sonication chamber.

Using a sonication chamber for ultrasonic vibrations in an ultrasonic mist inhaler allows the combination of the liquid chamber and the sonication chamber into the liquid reservoir structure.

It is noted that the expression "mist" used in the invention means the liquid is not heated as usually in traditional inhalers known from the prior art. In fact, traditional inhalers use heating elements to heat the liquid above its boiling temperature to produce a vapor, which is different from a mist.

In fact, when sonicating liquids at high intensities, the sound waves that propagate into the liquid media result in alternating high-pressure (compression) and low-pressure (rarefaction) cycles, at different rates depending on the frequency. During the low-pressure cycle, high-intensity ultrasonic waves create small vacuum bubbles or voids in the liquid. When the bubbles attain a volume at which they can no longer absorb energy, they collapse violently during a high-pressure cycle. This phenomenon is termed cavitation. During the implosion very high pressures are reached locally. At cavitation, broken capillary waves are generated, and tiny droplets break the surface tension of the liquid and are quickly released into the air, taking mist form.

In the ultrasonic mist inhaler, the liquid reservoir structure may comprise an internal bore providing an air passage from the sonication chamber toward the surroundings.

In the ultrasonic mist inhaler, the liquid reservoir structure may comprise a peripheral inner chamber arranged between the liquid chamber and the internal bore, the peripheral inner chamber providing the fluid communication between the liquid chamber and the sonication chamber.

In the ultrasonic mist inhaler, the liquid reservoir structure may be made in one piece.

In the ultrasonic mist inhaler, the peripheral inner chamber may comprise an inner wall delimiting the peripheral inner chamber and the liquid chamber.

In the ultrasonic mist inhaler, the peripheral inner chamber may comprise an outer wall delimiting the peripheral inner chamber and the liquid chamber.

In the ultrasonic mist inhaler, the outer wall may comprise at least an aperture providing fluid communication between the liquid chamber and the peripheral inner chamber.

In the ultrasonic mist inhaler, the peripheral inner chamber may comprise a circular opening providing fluid communication between the peripheral inner chamber and the sonication chamber.

In the ultrasonic mist inhaler, the inner wall may extend in the sonication chamber.

In the ultrasonic mist inhaler, a capillary element may be arranged between the liquid chamber and the sonication chamber.

In the ultrasonic mist inhaler, the peripheral inner chamber may comprise the capillary element.

Such arrangement of the capillary element forms a wick and prevents uncontrolled leaking of liquid out of the liquid chamber.

Preferably, the capillary element is wrapped into the peripheral inner chamber around the internal bore.

The capillary element may be a gauze. The capillary element may be formed of bamboo fibers, preferably in 100% bamboo fibers, or cotton, silica, tobacco cotton, or any combination of such material.

In the ultrasonic mist inhaler, the capillary element may have a U-shape cross section.

In the ultrasonic mist inhaler, the capillary element may insert into the peripheral inner chamber from the circular opening.

In the ultrasonic mist inhaler, the sonication chamber comprises means of ultrasonic vibrations.

The expression "means of ultrasonic vibrations" is similar to the expression "ultrasonic oscillation component" used in the patent application PCT/IB2019/055192.

Preferably, the two lateral portion of the U-shape cross section are inserted into peripheral inner chamber and the central portion is in surface contact with the means of ultrasonic vibrations.

In the ultrasonic mist inhaler, the circular opening of the peripheral inner chamber may face the means of ultrasonic vibrations.

In the ultrasonic mist inhaler, the means of ultrasonic vibrations are supported by an elastic member.

The elastic member is formed from an annular plate-shaped rubber.

The elastic member has an inner hole wherein a groove is designed for maintaining the means of ultrasonic vibrations.

In this case, since the elastic member is in line contact with the means of ultrasonic vibrations, suppression of vibrations of the liquid reservoir structure can more effectively be prevented. Thus, fine particles of the liquid atomized by the atomizing member can be sprayed farther.

In the ultrasonic mist inhaler, a high-frequency voltage may be applied to the means of ultrasonic vibrations to ultrasonically vibrate the means of ultrasonic vibrations, whereby a liquid supplied to a portion of the means of ultrasonic vibrations can be atomized and sprayed.

According to the ultrasonic mist inhaler, fine particles of the liquid atomized by the means of ultrasonic vibrations having a relatively small size can be sprayed farther.

Such means of ultrasonic vibrations may be a transducer preferably designed in a circular plate-shape. The material of the piezoelectric transducer is preferably in ceramic.

In the ultrasonic mist inhaler, the internal bore may have a mechanical spring.

Preferably, the mechanical spring pushes the central portion of the capillary element onto the means of ultrasonic vibrations to ensure the surface contact.

In the ultrasonic mist inhaler, the sonication chamber may have a bottom plate closing the sonication chamber.

In the ultrasonic mist inhaler, the bottom plate may be configured to support the elastic member.

In the ultrasonic mist inhaler, the bottom plate may be arranged to receive connectors for powering the means of ultrasonic vibrations.

In the ultrasonic mist inhaler, a first connector and a second connector, the first connector is a spring-loaded contact probe and the second connector is a side pin crossing the elastic member. A spring-loaded contact probe provides a permanent contact with the means of ultrasonic vibrations.

Preferably, a metal plate ensures electrical contact between the second connector and the means of ultrasonic vibrations.

In the ultrasonic mist inhaler, the liquid reservoir structure may have a top end comprising an airway fluidically coupled to the internal bore and configured to allow liquid mist to flow out of the airway.

In the ultrasonic mist inhaler, the liquid reservoir structure may be arranged between a mouthpiece and a casing housing electrical components for powering and operating the inhaler.

The bottom plate is sealed, thus preventing leakage of liquid from the sonication chamber to the casing.

In the ultrasonic mist inhaler, the top end of the liquid reservoir structure may be coupled with the mouthpiece, the mouthpiece being configured to allow suction of liquid mist flowing out of the airway to the surroundings.

Advantageously, the liquid reservoir structure is detachable from the mouthpiece and the casing.

The liquid reservoir structure and the mouthpiece or the casing may include complimentary arrangements for engaging with one another; further such complimentary arrangements may include; a bayonet type arrangement; a threaded engaged type arrangement; a magnetic arrangement; and, a friction fit arrangement; wherein the liquid reservoir structure includes a portion of the arrangement and the mouthpiece or the casing includes the complimentary portion of the arrangement.

Such design permits the liquid reservoir structure to be disposable. The liquid reservoir structure may be removed and reinstalled when required; a feature that gives the user the freedom to interchange flavors without the limitation of either completely using or having to discard unused liquid.

Further, such design eliminates the risk of fatigue of the means of ultrasonic vibrations in the sonication chamber and has a disposable means of ultrasonic vibrations which prevents the risk of fatigue and a disposable capillary element which prevents the risk of mixing flavor.

In the ultrasonic mist inhaler, an integrated circuit may be coupled to the bottom end of the liquid reservoir structure and communicatively coupled to the means of ultrasonic vibrations, the integrated circuit configured to cause the means of ultrasonic vibrations to vibrate.

Preferably, the means of ultrasonic vibrations is in electrical communication with an integrated circuit, preferably via the connectors.

Advantageously, the integrated circuit is designed to convert a direct current into an alternate current at high frequency.

The means of ultrasonic vibrations may be powered from electrical components of the casing through the connectors.

Preferably, the casing is configured to contain an electrical storage device and may encase at least a portion of the integrated circuit.

The casing may have all features described in the patent application PCT/IB2019/055192.

The ultrasonic mist inhaler according to the invention, wherein said liquid to be received in the liquid chamber comprises 57-70% (w/w) vegetable glycerin and 30-43% (w/w) propylene glycol, said propylene glycol including nicotine and flavorings.

An ultrasonic mist inhaler or a personal ultrasonic atomizer device, comprising:

- a liquid reservoir structure comprising a liquid chamber or cartridge adapted to receive liquid to be atomized,
- a sonication chamber in fluid communication with the liquid chamber or cartridge, wherein said liquid to be received in the liquid chamber comprises 57-70% (w/w) vegetable glycerin and 30-43% (w/w) propylene glycol, said propylene glycol including nicotine and flavorings.

BRIEF DESCRIPTION OF THE DRAWINGS

Some embodiments are illustrated by way of example and not limitation in the figures of the accompanying drawings.

DETAILED DESCRIPTION

The foregoing summary, as well as the following detailed description of certain embodiments of the present invention, will be better understood when read in conjunction with the appended drawings.

As used herein, an element recited in the singular and preceded with the word "a" or "an" should be understood as not excluding plural of said elements, unless such exclusion is explicitly stated. Furthermore, the references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The present invention is directed to an ultrasonic mist inhaler. The description of the invention and accompanying figures will be directed to the electronic vaporizing inhaler embodiment; however, other embodiments are envisioned, such as an inhaler for hookah, flavored liquids, medicine, and herbal supplements. Additionally, the device can be packaged to look like an object other than a cigarette. For instance, the device could resemble another smoking instrument, such as a pipe, water pipe, or slide, or the device could resemble another non-smoking related object.

Ultrasonic mist inhalers are either disposable or reusable. The term "reusable" as used herein implies that the energy storage device is rechargeable or replaceable or that the liquid is able to be replenished either through refilling or through replacement of the liquid reservoir structure. Alternatively, in some embodiments reusable electronic device is both rechargeable and the liquid can be replenished. A disposable embodiment will be described first, followed by a description of a reusable embodiment.

Conventional electronic vaporizing inhaler tend to rely on inducing high temperatures of a metal component configured to heat a liquid in the inhaler, thus vaporizing the liquid that can be breathed in. The liquid typically contains nicotine and flavorings blended into a solution of propylene glycol (PG) and vegetable glycerin (VG), which is vaporized vi a heating component at high temperatures. Problems with conventional inhaler may include the possibility of burning metal and subsequent breathing in of the metal along with the burnt liquid. In addition, some may not prefer the burnt smell or taste caused by the heated liquid.

In contrast, aspects of the present disclosure include an ultrasonic mist inhaler that atomizes the liquid through ultrasonic vibrations, which produces micro water bubbles in the liquid. When the bubbles come into contact with ambient air molecules, water droplets of about 0.25 to 0.5 microns spray into the air, thereby generating micro-droplets that can be absorbed through breathing, similar to breathing in a mist.

No heating elements are involved, thereby leading to no burnt elements and reducing second-hand smoke effects.

Figure 1:
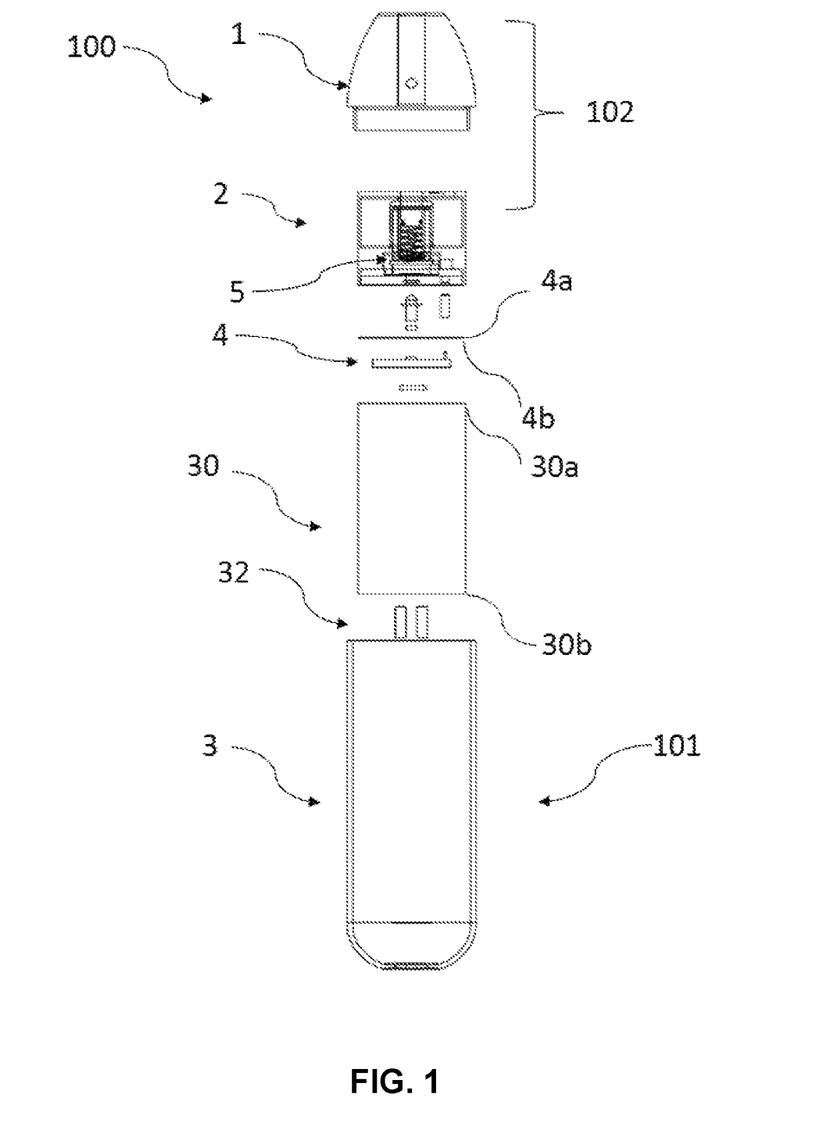
FIG. 1 is an exploded view of components of the ultrasonic mist inhaler according to an embodiment of the invention.

FIG. 1 depicts a disposable ultrasonic mist inhaler embodiment 100 of the invention. As can be seen in FIG. 1, the ultrasonic mist inhaler 100 has a cylindrical body with a relatively long length "L" as compared to the diameter "D." In terms of shape and appearance, the ultrasonic mist inhaler 100 is designed to mimic the look of a typical cigarette. For instance, the inhaler can feature a first portion 101 that primarily simulates the tobacco rod portion of a cigarette and a second portion 102 that primarily simulates a filter. In the disposable embodiment of the invented device, the first portion and second portion are regions of a single, but-separable device. The designation of a first portion and a second portion is used to conveniently differentiate the components that are primarily contained in each portion.

As can be seen in FIG. 1, the ultrasonic mist inhaler comprises a mouthpiece 1, a liquid reservoir structure 2 and a casing 3. The first portion 101 comprises the casing 3 and the second portion 102 comprises the mouthpiece 1 and the reservoir structure 2.

The first portion 101 contains the power supply energy.

An electrical storage device 30 powers the ultrasonic mist inhaler 100. The electrical storage device 30 can be a battery, including but not limited to a lithium-ion, alkaline, zinc-carbon, nickel-metal hydride, or nickel-cadmium battery; a super capacitor; or a combination thereof. In the disposable embodiment, the electrical storage device 30 is not rechargeable, but, in the reusable embodiment, the electrical storage device 30 would be selected for its ability to recharge. In the disposable embodiment, the electrical storage device 30 is primarily selected to deliver a constant voltage over the life of the inhaler 100. Otherwise, the performance of the inhaler would degrade over time. Preferred electrical storage devices that are able to provide a consistent voltage output over the life of the device include lithium-ion and lithium polymer batteries.

The electrical storage device 30 has a first end 30*a* that generally corresponds to a positive terminal and a second end 30*b* that generally corresponds to a negative terminal. The negative terminal is extending to the first end 30*a*.

Because the electrical storage device 30 is located in the first portion 101 and the liquid reservoir structure 2 is located in the second portion 102, the joint needs to provide electrical communication between those components. In the present invention, electrical communication is established using at least an electrode or probe that is compressed together when the first portion 101 is tightened into the second portion 102.

In order for this embodiment to be reusable, the electrical storage device 30 is rechargeable. The casing 3 contains a charging port 32.

The integrated circuit 4 has a proximal end 4*a* and a distal end 4*b*. The positive terminal at the first end 30*a* of the electrical storage device 30 is in electrical communication with a positive lead of the flexible integrated circuit 4. The negative terminal at the second end 30*b* of the electrical storage device 30 is in electrical communication with a negative lead of the integrated circuit 4. The distal end 4*b* of the integrated circuit 4 comprise a microprocessor. The microprocessor is configured to process data from a sensor, to control a light, to direct current flow to means of ultrasonic vibrations 5 in the second portion 102, and to terminate current flow after a preprogrammed amount of time.

The sensor detects when the ultrasonic mist inhaler 100 is in use (when the user draws on the inhaler) and activates the microprocessor. The sensor can be selected to detect changes in pressure, air flow, or vibration. In a preferred embodiment, the sensor is a pressure sensor. In the digital embodiment, the sensor takes continuous readings which in turn requires the digital sensor to continuously draw current, but the amount is small and overall battery life would be negligibly affected.

Additionally, the integrated circuit 4 may comprise a H bridge, preferably formed by 4 MOSFETs to convert a direct current into an alternate current at high frequency.

Figure 2:
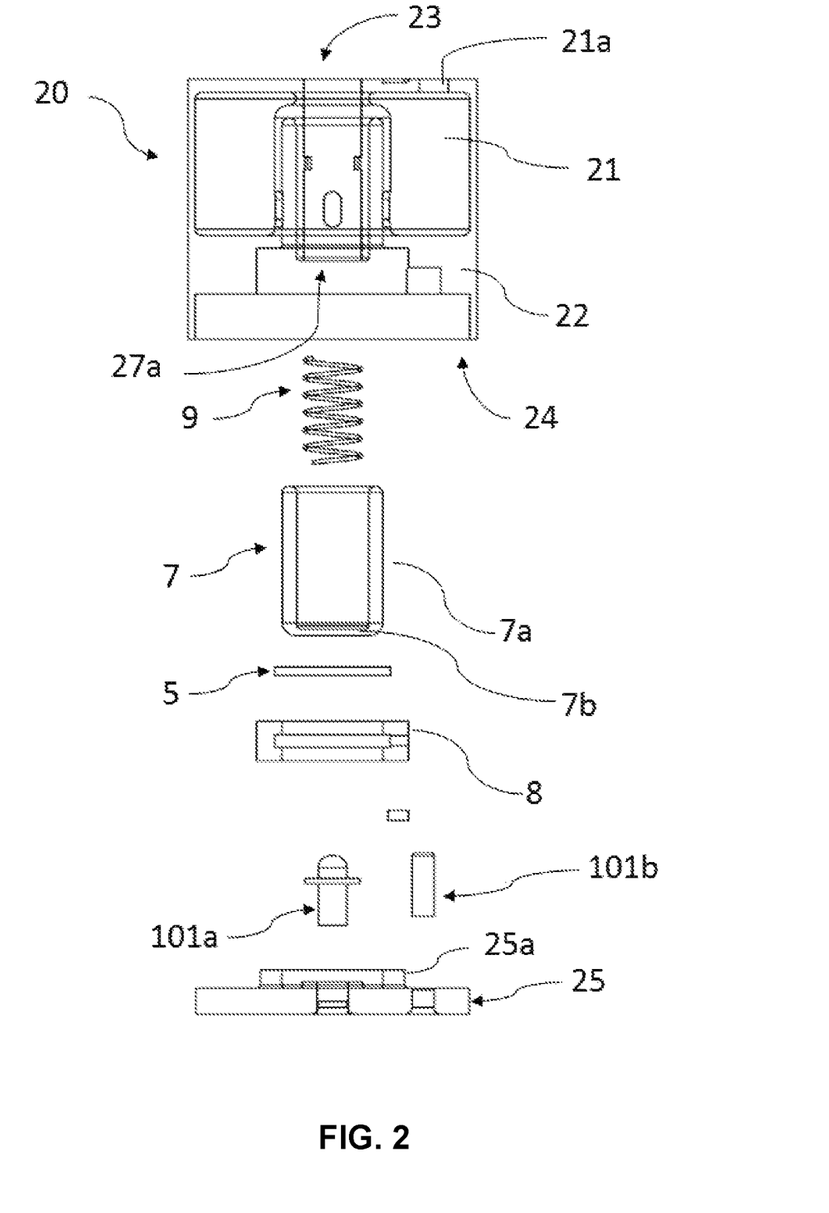
FIG. 2 is an exploded view of components of the inhaler liquid reservoir structure according to an embodiment of the invention.
Figure 3:
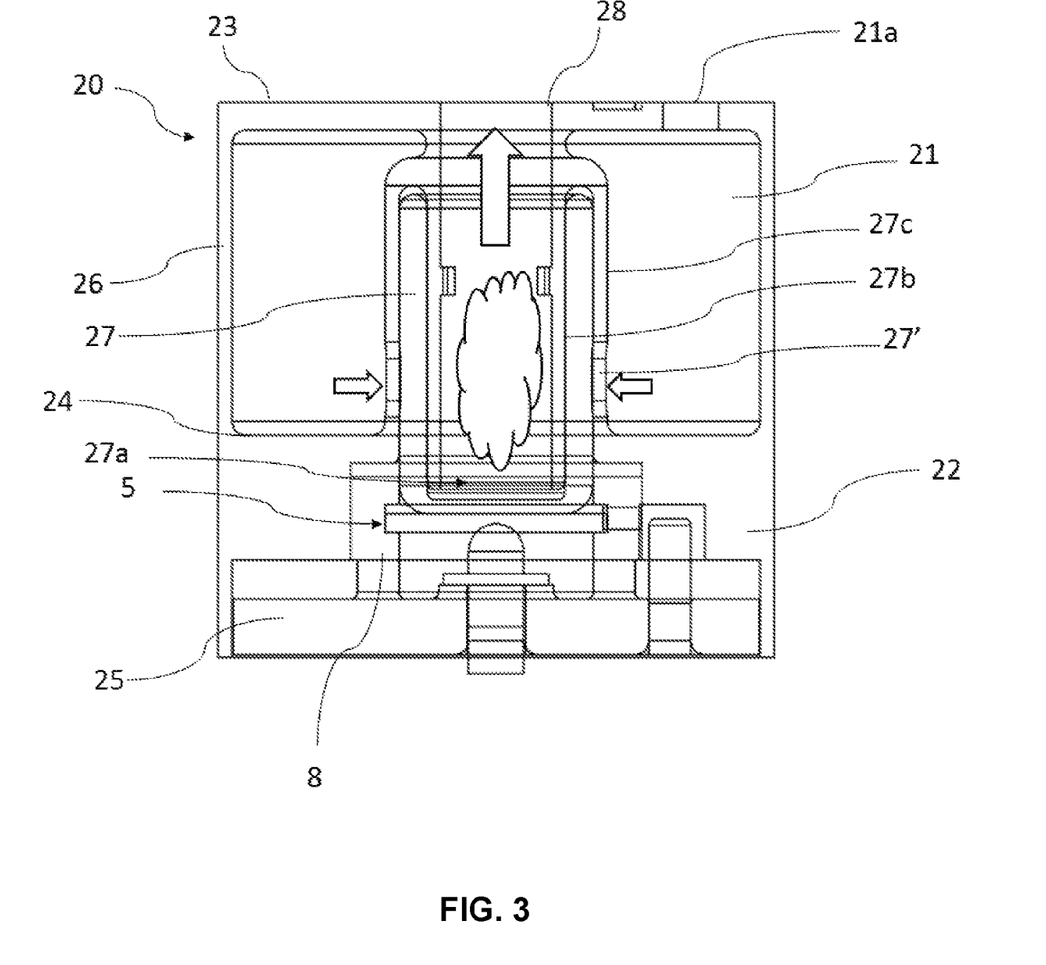
FIG. 3 is a cross-section view of components of the inhaler liquid reservoir structure according to FIG. 1.

Referring to FIG. 2 and FIG. 3, illustrations of a liquid reservoir structure 2 according to an embodiment are shown. The liquid reservoir structure 2 comprises a liquid chamber 21 adapted to receive liquid to be atomized and a sonication chamber 22 in fluid communication with the liquid chamber 21.

In the embodiment shown, the liquid chamber 21 and sonication chamber 22 are part of a single assembly wherein a liquid is incorporated in the liquid chamber 21 from an inlet opening 21a.

As an example of sensor position, the sensor may be located in the sonication chamber.

The liquid reservoir structure 2 is arranged between the mouthpiece 1 and the casing 3 and is detachable from the mouthpiece 1 and the casing 3.

The liquid reservoir structure 2 and the mouthpiece 1 or the casing 3 may include complimentary arrangements for engaging with one another; further such complimentary arrangements may include one of the following: a bayonet type arrangement; a threaded engaged type arrangement; a magnetic arrangement; and, a friction fit arrangement; wherein the liquid reservoir structure 2 includes a portion of the arrangement and the mouthpiece 1 or the casing 3 includes the complimentary portion of the arrangement.

In the reusable embodiment, the components are substantially the same. The differences in the reusable embodiment vis-a-vis the disposable embodiment are the accommodations made to replace the liquid reservoir structure 2.

As shown in FIG. 3, the liquid reservoir structure 2 has a top wall 23, a middle wall 24 and a bottom wall 25 extending from a perimeter wall 26.

The top wall 23 and the middle wall 24 with the perimeter side 26 defines the outer of the liquid chamber 21. The middle wall 24 and the bottom wall 25 define with the perimeter wall 26 the outer of the sonication chamber 22. It means the middle wall 24 is a common wall with the liquid chamber 21 and the sonication chamber 22.

The liquid reservoir structure 2 has an internal bore 28 providing an air passage from the sonication chamber 21 toward the surroundings.

Further, the liquid reservoir structure 2 comprises of a peripheral inner chamber 27 arranged between the liquid chamber 21 and the internal bore 28. The peripheral inner chamber 27 provides the fluid communication between the liquid chamber 21 and the sonication chamber 22.

The peripheral inner chamber 27 has an outer wall 27c delimiting the peripheral inner chamber 27 and the liquid chamber 21. The peripheral inner chamber 27 further has an inner wall 27b delimiting the peripheral inner chamber 27 and the internal bore 28. More particularly, the internal bore 28 is formed by the inner wall 27b.

The outer wall 27c defines a plurality of transversely extending apertures 27'. The apertures 27' create capillaries from the liquid chamber 21 through the thickness of the peripheral inner chamber 27 to the sonication chamber 22. The apertures 27' can vary in diameter (the diameter of the capillary aperture will be dictated to a large extent by the viscosity of the fluid; a more viscous fluid can have a larger diameter capillary without leaking, while a less viscous fluid requires a smaller diameter capillary). Generally speaking, the diameters of the apertures 27' are sufficient to facilitate passage of the not yet mist fluid. The apertures 27' can be circular or any other of a variety of geometric shapes.

A circular opening 27a of the peripheral inner chamber 27 provides fluid communication between the peripheral inner chamber 27 and the sonication chamber 22.

The inner wall 27c of the peripheral inner chamber 27 extends beyond in the sonication chamber 22.

The top wall 23 of the liquid reservoir structure 2 comprises an airway fluidically coupled to the internal bore 28 and configured to allow liquid mist to flow out of the airway.

The top wall 23 of the liquid reservoir structure 2 may be coupled with the mouthpiece 1 and the mouthpiece 1 is configured to allow suction of mist liquid flowing out of the airway to the surroundings.

The bottom wall 25 of the liquid reservoir structure 2 is a bottom plate 25 closing the sonication chamber 22 so that the liquid reservoir structure 2 comprises the sonication chamber 22. The bottom plate 25 is sealed, thus preventing leakage of liquid from the sonication chamber 22 to the casing 3.

The peripheral inner chamber 27 defines a cavity. As depicted in FIG. 3, inserted into the cavity and in contact with the apertures 27' is a capillary element 7. The capillary element 7 absorbs liquid from the liquid chamber 21 through the apertures 27'. The capillary element 7 is a wick. The capillary element 7 transports liquid to the sonication chamber 22 via capillary action. Preferably the capillary element 7 is made of bamboo fibers; however, cotton, paper, or other fiber strands could be used for a wick material.

In one embodiment of the ultrasonic mist inhaler 100, the capillary element 7 has a U-shape cross section with two lateral portion 7a inserted into peripheral inner chamber 27 and a central portion 7b in surface contact with the means of ultrasonic vibrations 5.

As can be seen in FIG. 3, the means of ultrasonic vibrations 5 are disposed directly below the capillary element 7.

The circular opening 27a of the peripheral inner chamber 27 faces the means of ultrasonic vibrations 5.

The means of ultrasonic vibrations 5 may be a transducer. For example, the means of ultrasonic vibrations 5 may be a piezoelectric transducer, preferably designed in a circular plate-shape. The material of the piezoelectric transducer is preferably in ceramic.

A variety of transducer materials can also be used for the means of ultrasonic vibrations 5.

The means of ultrasonic vibrations 5 are supported by an elastic member 8. The elastic member 8 is formed from an annular plate-shaped rubber having an inner hole 8' wherein a groove is designed for maintaining the means of ultrasonic vibrations 5.

The bottom plate 25 has a protruding portion 25a on which the elastic member 8 is disposed so that the protruding 25a is inserted at least partially into the elastic member annular plate.

The bottom plate 25 is fixed to the liquid reservoir structure 2 by means of fixation such as screws, glue or friction.

As depicted in FIG. 3, the elastic member is in line contact with the means of ultrasonic vibrations 5 and prevents contact between the means of ultrasonic vibrations 5 and the inhaler walls, suppression of vibrations of the liquid reservoir structure are more effectively prevented. Thus, fine particles of the liquid atomized by the atomizing member can be sprayed farther.

The internal bore comprises a mechanical spring 9.

By pushing the capillary element 7*b* onto the means of ultrasonic vibrations 5, the mechanical spring 9 ensures a contact surface between them.

The means of ultrasonic vibrations 5 are in electrical communication with electrical contactors 101*a*, 101*b*. It is noted that, the distal end 4*b* of the integrated circuit 4 has an inner electrode and an outer electrode. The inner electrode contacts the first electrical contact 101*a* which is a spring contact probe, and the outer electrode contacts the second electrical contact 101*b* which is a side pin. Via the integrated circuit 4, the first electrical contact 101*a* is in electrical communication with the positive terminal of the electrical storage device 30 by way of the microprocessor, while the second electrical contact 101*b* is in electrical communication with the negative terminal of the electrical storage device 30.

The electrical contacts 101*a*, 101*b* crossed the bottom plate 25. The bottom plate 25 is designed to be received inside the perimeter wall 26 of the liquid reservoir structure 2. The bottom plate 25 rests on complementary ridges, thereby creating the sonication chamber 21.

The liquid reservoir structure 2 and the bottom plate 25 can be made using a variety of thermoplastic materials.

When the user draws on the ultrasonic mist inhaler 100, the liquid is drawn from the reservoir chamber 21 by capillarity, through the plurality of apertures 27', and into the capillary element 7. The capillary element 7 brings the liquid into contact with the means of ultrasonic vibrations 5 of the inhaler 100. The user's draw also causes the pressure sensor to activate the integrated circuit 4, which directs current to the means of ultrasonic vibrations 5. Thus, when the user draws on the mouthpiece 1 of the inhaler 100, two actions happen at the same time. Firstly, the sensor activates the integrated circuit 4, which triggers the means of ultrasonic vibrations 5 to begin vibrating. Secondly, the draw reduces the pressure outside the reservoir chamber 21 such that flow of the liquid through the apertures 27' begins, which saturates the capillary element 7. The capillary element 7 transports the liquid to the means of ultrasonic vibrations 5, which causes bubbles to form in a capillary channel by the means of ultrasonic vibrations 5 and mist the liquid. Then, the mist liquid is drawn by the user.

The ultrasonic mist inhaler 100 of the present disclosures is a more powerful version of current portable medical nebulizers, in the shape and size of current e-cigarettes and with a particular structure for effective vaporization. It is a healthier alternative to cigarettes and current e-cigarettes products.

The ultrasonic mist inhaler 100 of the present disclosures has particular applicability for those who use electronic inhalers as a means to quit smoking and reduce their nicotine dependency. The ultrasonic mist inhaler 100 provides a way to gradually taper the dose of nicotine.

Other embodiments of the invented ultrasonic mist inhaler 100 are easily envisioned, including medicinal delivery devices.

It is to be understood that the above description is intended to be illustrative, and not restrictive. For example, the above-described embodiments may be used in combination with each other. In addition, many modifications may be made to adapt a particular situation or material to the teachings of the invention without departing from its scope.

The invention claimed is:

1. An ultrasonic mist inhaler, comprising:

a liquid reservoir structure comprising:

a liquid chamber adapted to receive liquid to be atomized;

a sonication chamber in fluid communication with the liquid chamber, an internal bore providing an air passage from the sonication chamber toward the surroundings; and a peripheral inner chamber arranged between the liquid chamber and the internal bore, the peripheral inner chamber including a capillary element to conduct liquid from the liquid chamber to the sonication chamber to provide the fluid communication between the liquid chamber and the sonication chamber.

2. The ultrasonic mist inhaler according to claim 1, wherein the peripheral inner chamber comprises an outer wall delimiting the peripheral inner chamber and the liquid chamber.

3. The ultrasonic mist inhaler according to claim 2, wherein the outer wall comprises at least an aperture providing fluid communication between the liquid chamber and the peripheral inner chamber.

4. The ultrasonic mist inhaler according to claim 1, wherein the peripheral inner chamber comprises a circular opening providing fluid communication between the peripheral inner chamber and the sonication chamber.

5. The ultrasonic mist inhaler according to claim 1, wherein the peripheral inner chamber comprises an inner wall delimiting the peripheral inner chamber and the liquid chamber.

6. The ultrasonic mist inhaler according to claim 5, wherein the inner wall extends in the sonication chamber.

7. The ultrasonic mist inhaler according to claim 1, wherein the liquid reservoir structure is made in one piece.

8. The ultrasonic mist inhaler according to claim 1, wherein the sonication chamber comprises an ultrasonic vibration device.

9. The ultrasonic mist inhaler according to claim 8, wherein the ultrasonic vibration device is supported by an elastic member.

10. The ultrasonic mist inhaler according to claim 1, wherein the internal bore has a mechanical spring.

11. The ultrasonic mist inhaler according to claim 1, wherein the liquid reservoir structure comprises a top end comprising an airway fluidically coupled to the internal bore and configured to allow liquid mist to flow out of the airway.

12. The ultrasonic mist inhaler according to claim 1, the liquid reservoir structure is arranged between a mouthpiece and a casing housing electrical components for powering and operating the inhaler.

13. The ultrasonic mist inhaler according to claim 1, wherein the liquid chamber contains a liquid comprising 57-70% (w/w) vegetable glycerin and 30-43% (w/w) propylene glycol, the propylene glycol including nicotine and flavorings.

* * * * *